US009480674B2

(12) United States Patent
Saurat

(10) Patent No.: US 9,480,674 B2
(45) Date of Patent: Nov. 1, 2016

(54) METHOD AND COMPOSITION FOR TREATING ACNE

(71) Applicant: Jean Hilaire Saurat, Geneva (CH)

(72) Inventor: Jean Hilaire Saurat, Geneva (CH)

(73) Assignee: THESAN PHARMACEUTICALS, INC., Carlsbad, CA (US)

( * ) Notice: Subject to any disclaimer, the term of this patent is extended or adjusted under 35 U.S.C. 154(b) by 0 days.

(21) Appl. No.: 14/536,507

(22) Filed: Nov. 7, 2014

(65) Prior Publication Data

US 2015/0057343 A1 Feb. 26, 2015

Related U.S. Application Data

(63) Continuation-in-part of application No. PCT/IB2013/053979, filed on May 15, 2013.

(60) Provisional application No. 62/041,751, filed on Aug. 26, 2014, provisional application No. 62/034,005, filed on Aug. 6, 2014.

(30) Foreign Application Priority Data

May 15, 2012 (EP) .................................... 12168121

(51) Int. Cl.
| | | |
|---|---|---|
| *A61K 31/352* | (2006.01) | |
| *A61K 47/10* | (2006.01) | |
| *A61K 45/06* | (2006.01) | |
| *A61K 9/00* | (2006.01) | |
| *G01N 33/68* | (2006.01) | |
| *G01N 33/50* | (2006.01) | |

(52) U.S. Cl.
CPC ............. *A61K 31/352* (2013.01); *A61K 45/06* (2013.01); *A61K 47/10* (2013.01); *G01N 33/5088* (2013.01); *G01N 33/6893* (2013.01); *A61K 9/0014* (2013.01); *G01N 2800/20* (2013.01)

(58) Field of Classification Search
CPC ..................... G01N 33/5088; G01N 33/6893; G01N 2800/20; A61K 31/352; A61K 47/10; A61K 45/06; A61K 9/0014
See application file for complete search history.

(56) References Cited

U.S. PATENT DOCUMENTS 6,902,881 B2 * 6/2005 Falchuk .................... 435/1.1
2003/0166583 A1 9/2003 Yoa-Pu Hu et al.

FOREIGN PATENT DOCUMENTS

| DE | 10 2006 011747 A1 | 9/2007 | |
|---|---|---|---|
| KR | 1020110139397 A * | 12/2011 | ............ A61K 31/35 |
| WO | WO 2007/110241 A1 | 10/2007 | |
| WO | WO 2009/093207 A1 | 7/2009 | |
| WO | WO 2011069860 A1 * | 6/2011 | |
| WO | WO 2013/171696 A1 | 11/2013 | |

OTHER PUBLICATIONS

KR 1020110139397 KIPO Machine Translation of Jul. 14, 2015, p. 1-18.*
Shimizu, S., The Laboratory Mouse, 2004, Chapter 32, Routes of Administration, p. 527-541.*
Chatuphonprasert, W.,"Suppression of beta-naphthoflavone induced CYP1A expression and lipid-peroxidation by berberine." Fitoterapia 82.6 (2011): 889-895.*
J.M. Rowe et al.: "Illuminating Role of CYP1A1 in Skin Function", *The Journal of Investigative Dermatology*, vol. 128, No. 7, Jul. 2008, pp. 1866-1868.
International Search Report issued by the International Searching Authority on Aug. 14, 2013 in conncetion with PCT International Application No. PCT/IB2013/053979.
Written Opinion of the International Searching Authority issued by the International Searching Authority on Nov. 15, 2014 in connection with PCT International Application No. PCT/IB2013/053979.
International Preliminary Report on Patentability issued by the International Bureau of WIPO on Nov. 18, 2014 in connection with PCT International Application No. PCT/IB2013/053979.
Official Action issued by the Chinese Patent Office on Aug. 5, 2015 in connection with Chinese Patent Application No. 201380025088.6.
Official Action issued by the New Zealand Patent Office on Oct. 22, 2015 in connection with New Zealand Patent Application No. 702357.

* cited by examiner

*Primary Examiner* — Samantha Shterengarts
*Assistant Examiner* — Matt Mauro
(74) *Attorney, Agent, or Firm* — John P. White; Gary J. Gershik; Cooper & Dunham LLP

(57) ABSTRACT

The subject invention provides a method of treating acne in a subject which comprises topically and periodically applying to the subject's acne a composition comprising 3-phenyl-1-benzo[f]chromen-1-one and a pharmaceutically acceptable carrier, wherein the 3-phenyl-1-benzo[f]chromen-1-one is present in an amount effective to treat the subject's acne. The subject invention also provides a method of treating a skin condition associated with abnormal sebum secretion or abnormal sebaceous gland function in a subject, compositions in such methods and a sorting method for identifying agonists of AhR pathway, useful in such methods and compositions.

43 Claims, 8 Drawing Sheets

METHOD AND COMPOSITION FOR TREATING ACNE

CROSS-REFERENCE TO RELATED APPLICATIONS

This application is a continuation-in-part of PCT International Application No. PCT/IB2013/053979, filed May 15, 2013, claiming priority of European Patent Application No. 12168121.7, filed May 15, 2012, and also claims the benefit of U.S. Provisional Applications Nos. 62/041,751, filed Aug. 26, 2014 and 62/034,005, filed Aug. 6, 2011, the contents of each of which are hereby incorporated by reference in their entirety.

Throughout this application, various publications are referred to by first author and year of publication. Full citations for these publications are presented in a List of References section immediately before the claims. Disclosures of the publications in the List of References in their entireties are hereby incorporated by reference into this application in order to more fully describe the state of the art as of the date of the invention described herein.

BACKGROUND

1. Field of the Invention

The present invention relates to triaging or sorting and selecting substances for their capacity for sebosuppressive activity in topical skin treatments. The invention also concerns substances identified from such triaging or sorting.

The present invention relates more particularly to a topical pharmaceutical composition for the treatment and/or prevention of hyperseborrhea and associated seborrheic skin disorders such as acne and seborrheic dermatitis.

2. Description of the Prior Art

The aryl hydrocarbon Receptor (AhR) is a transcription factor, which induces the expression of some genes while inhibiting the expression of other genes. A significant number of ligands, both naturally occurring ligands present in foods, as well as xenobiotics, have been reported to interact with this receptor (Abel et al. (2010)). AhR is typically expressed in epithelial and mesenchymal skin cells, as well as in other cell types (Ikuta et al. 2009). International Patent Publications WO 2004/041758 and WO 2007/128725 and U.S. Patent Application Publication No. 2009/0028804 A1 describe certain in vitro tests to determine the antagonist or agonist nature of such ligands.

The prototypical xenobiotic agonist ligand of the AhR is the notorious environmental toxin 2,3,7,8-tetrachlorodibenzo-p-dioxin (TCDD), better known simply as "dioxin" (Mandal (2005)). Other xenotoxic compounds which interact as agonists with the AhR are also capable of causing various types of damaging tissue lesions. Multiple toxic effects are known. The most visible are the cystic lesions formerly called "chloracne" but which have more recently been redefined as MADISH (Saurat et al. (2012)). For this reason, the use of AhR pathway agonists in a therapeutic and/or preventative context as active agents that beneficially modulate skin function is counter-intuitive. Indeed, International Patent Publications WO 2004/041758 and WO 2007/128725 propose to use AhR antagonists rather than agonists to treat various dermatological conditions, including acne.

U.S. Patent Application Publication No. 2010/0324109 A1 suggests that the application to the skin of certain AhR receptor pathway agonists may favorably modulate some skin functions such as sebaceous gland function, acne, defense against infection, wound healing, and skin atrophies which involve dermatoporosis and estrogen deprivation. However, to achieve a therapeutic window between the beneficial application of certain AhR pathway agonists and the detrimental effects of other AHR pathway agonists, such as TCDD, certain properties must be selected for.

It is currently unknown how to best identify suitable candidates from AhR agonists that are likely to be endowed with sebosuppressive properties and likely to be therapeutically beneficial to man. Currently available approaches comprise prolonged dosing with atrophy-inducing tests of the differentiated regions of the sebaceous glands in suitable animal species. These tests involve complex histological interpretation and, in addition, typically require the prolonged chronic application of the ligands under consideration.

It is therefore an objective of this invention to propose a triage or sorting method that is rapid, sensitive and predictive of human efficacy with respect to sebosuppressive properties on human skin. This invention thus provides a novel method to identify sebum reducing AhR pathway agonists useful to treat certain skin diseases, and novel pharmaceutical compositions useful for treating disorders related to abnormal metabolism mediated by the AhR receptor.

SUMMARY OF THE INVENTION

The subject invention provides a method of treating acne in a subject which comprises topically and periodically applying to the subject's acne a composition comprising 3-phenyl-1-benzo[f]chromen-1-one and a pharmaceutically acceptable carrier, wherein the 3-phenyl-1-benzo[f]chromen-1-one is present in an amount effective to treat the subject's acne.

The subject invention also provides a method of treating a skin condition associated with abnormal sebum secretion or abnormal sebaceous gland function in a subject which comprises topically and periodically applying to an area of subject's skin affected by the skin condition a composition comprising 3-phenyl-1-benzo[f]chromen-1-one and a pharmaceutically acceptable carrier, wherein the 3-phenyl-1-benzo[f]chromen-1-one is present in an amount effective to treat the skin condition.

The subject invention also provides a composition comprising 3-phenyl-1-benzo[f]chromen-1-one and a pharmaceutically acceptable carrier, wherein the 3-phenyl-1-benzo[f]chromen-1-one is present at a concentration between about 0.005% and about 5% by weight.

the progenitor cells (1A);
the undifferentiated cells (2A);
the differentiated cells (3A); and
the mature cells (4A).

Figure 2:
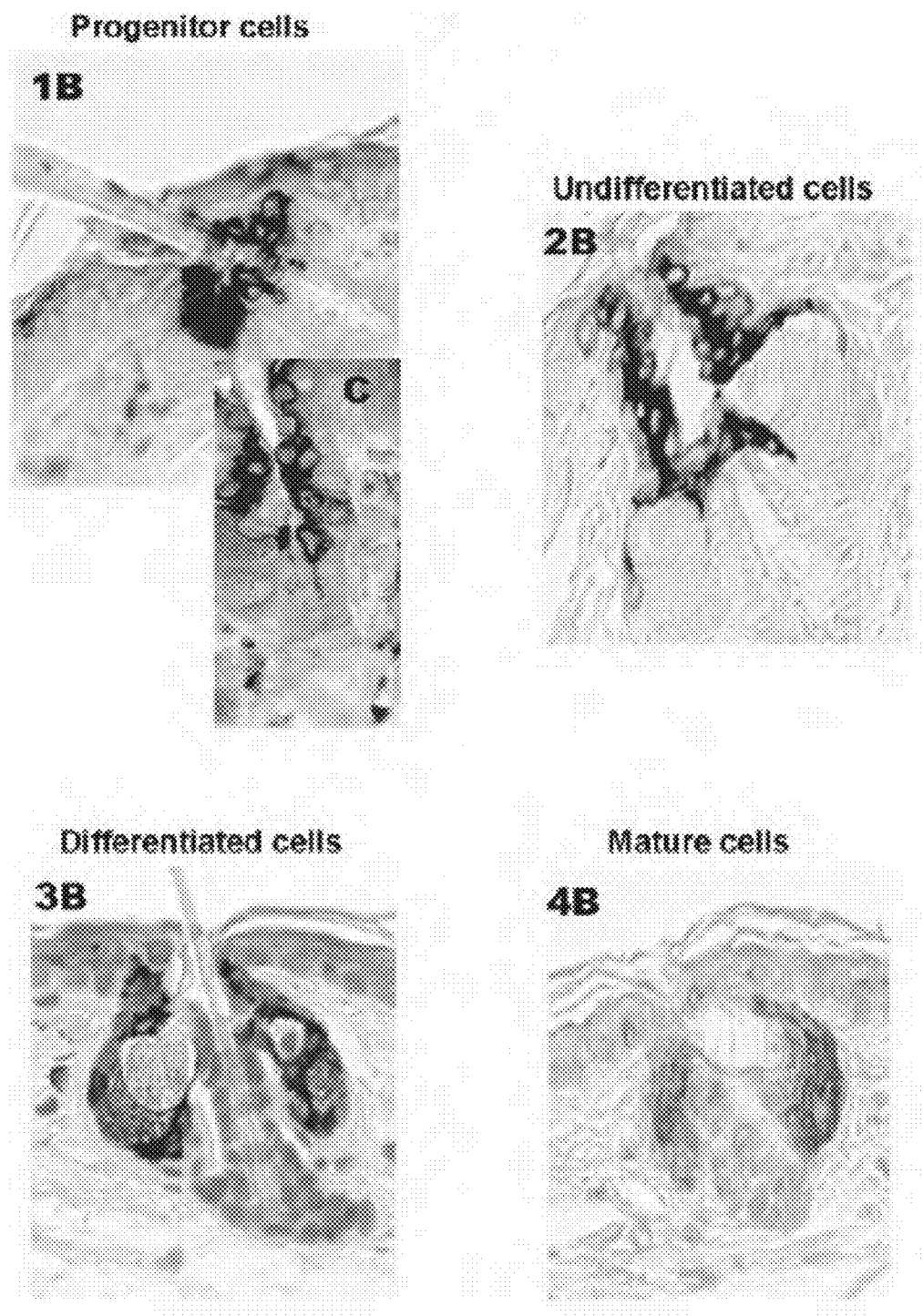

FIG. 2 shows photomicrographs (1B and C, 2B, 3B and 4B) identifying the four types of cells able to express the CYP1A1 gene, following treatment with Ahr pathway agonists. 1B and C show progenitor cells following administration of NSA4; 2B shows undifferentiated cells following treatment with NSA1; 3B shows differentiated cells following treatment with NSA2 and 4B shows mature cells following treatment with NSA3. Photograph C shows progenitor cells at a different viewing angle and magnification of the region shown in photograph 1B.

Figure 1:
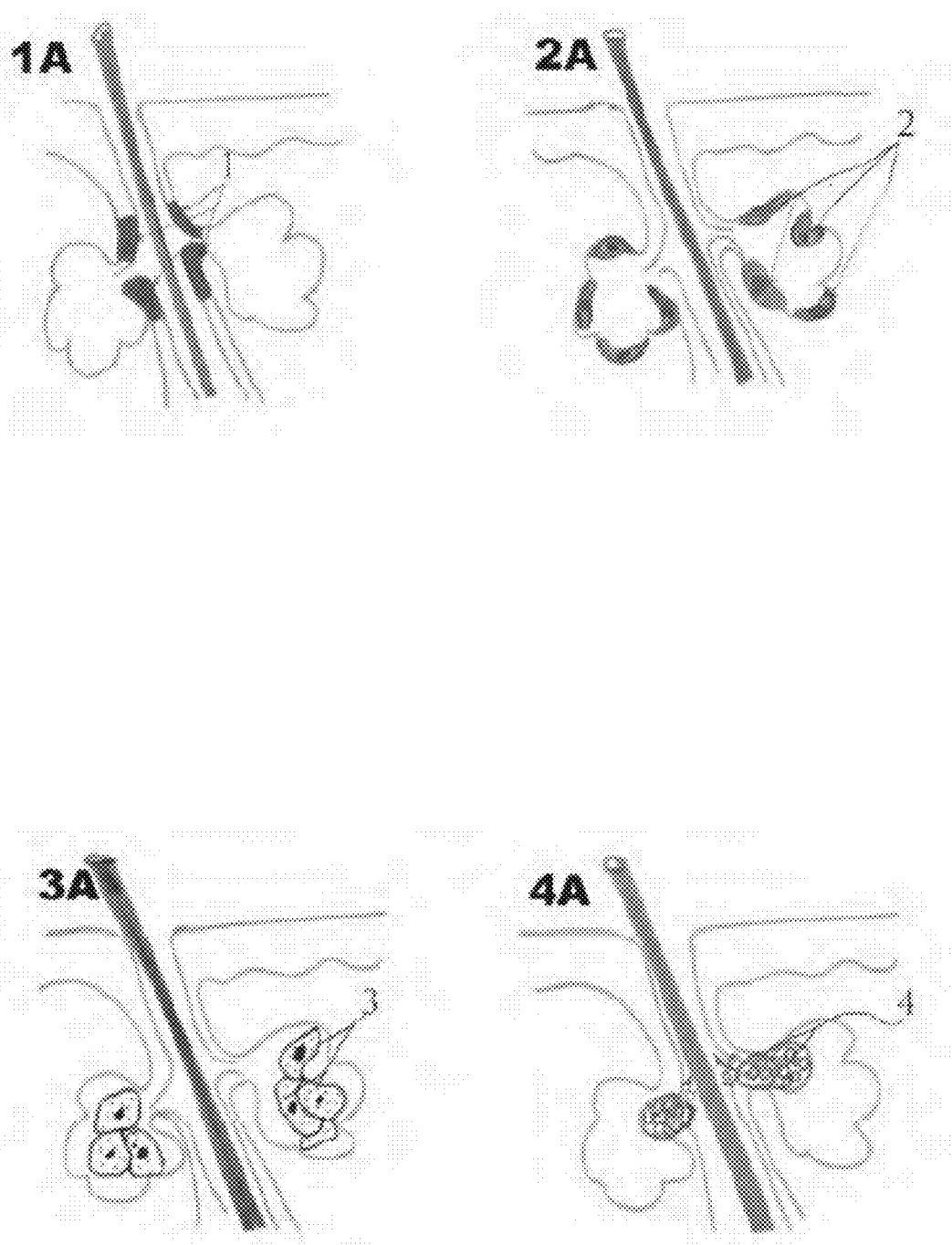
FIG. 1 provides illustrations (1A, 2A, 3A and 4A) identifying the location inside a sebaceous gland of the four types of sebaceous cells able to express the CYP1A1 gene, namely.
Figure 3:
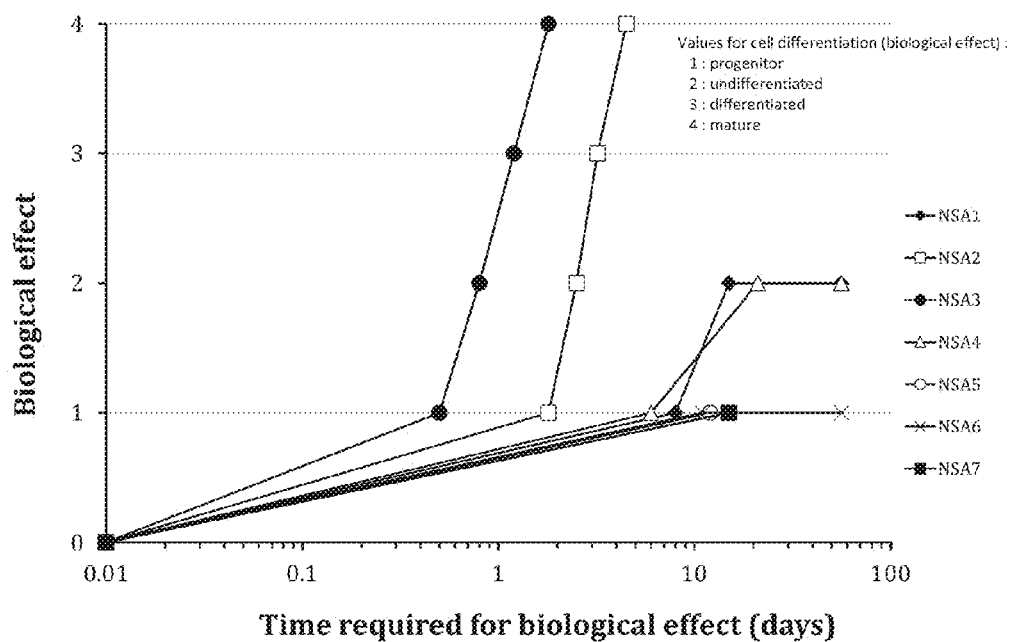

FIG. 3 shows the onset of CYP1A1 activity vs. time in all four sub-populations of sebaceous cells from FIGS. 1 and 2, after topical application of several ligands of the AhR receptor. In this figure, the biological effect is defined as the stage of sebaceous cell differentiation, signified by values of 1 to 4 corresponding to stage 1 to 4 of differentiation as discussed above; these effects are affected by exposure to test compounds as indicated in visualization of CYP1A1.

Figure 4:
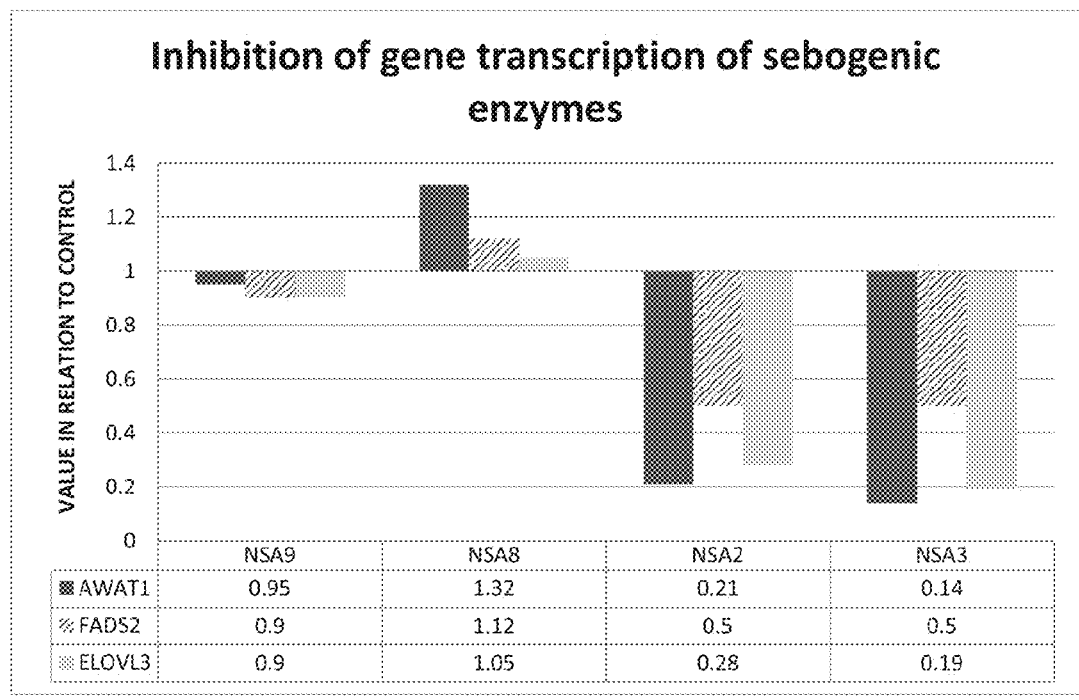

FIG. 4 shows the inhibition of the transcription of certain genes encoding sebogenic enzymes by three structurally related compounds (NSA-2, NSA-8 and NSA-9) and compared with NSA-3(TCDD).

Figure 5:
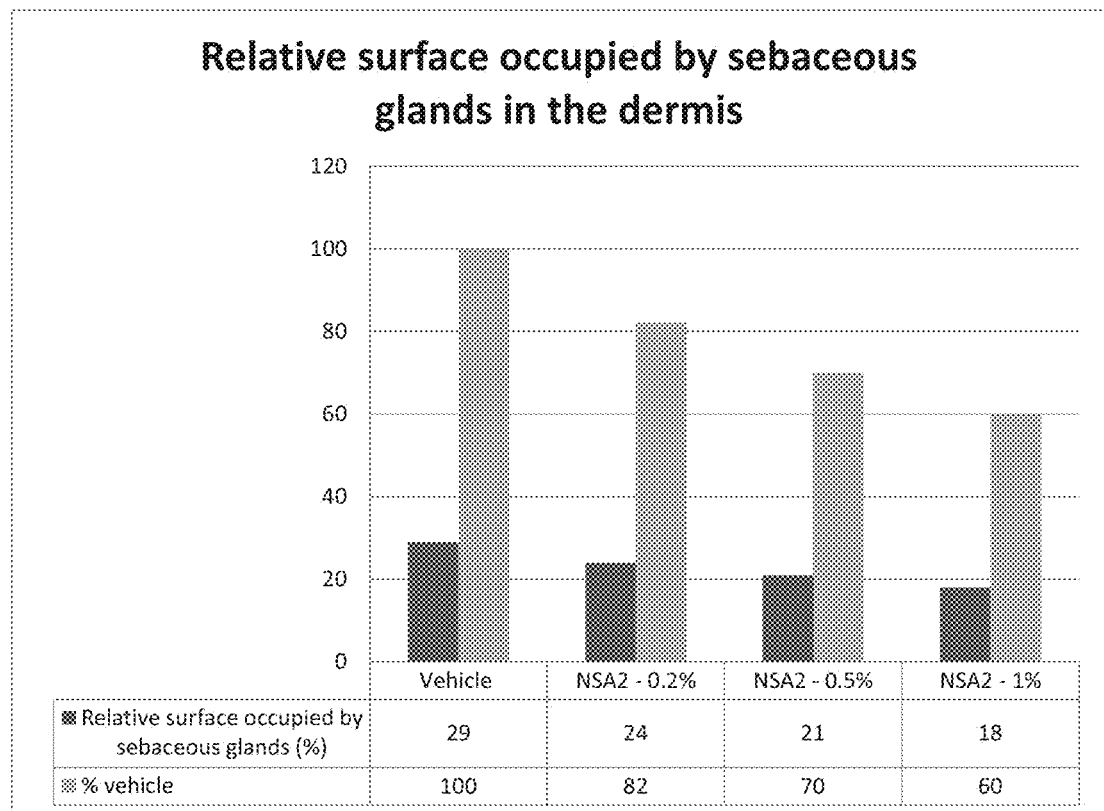

FIG. 5 shows the relative surface occupied by the sebaceous glands in the dermis over time, subsequent to treatment with NSA-2 (3-phenyl-1-benzo[f]chromen-1-one) at three different concentrations.

Figure 6:
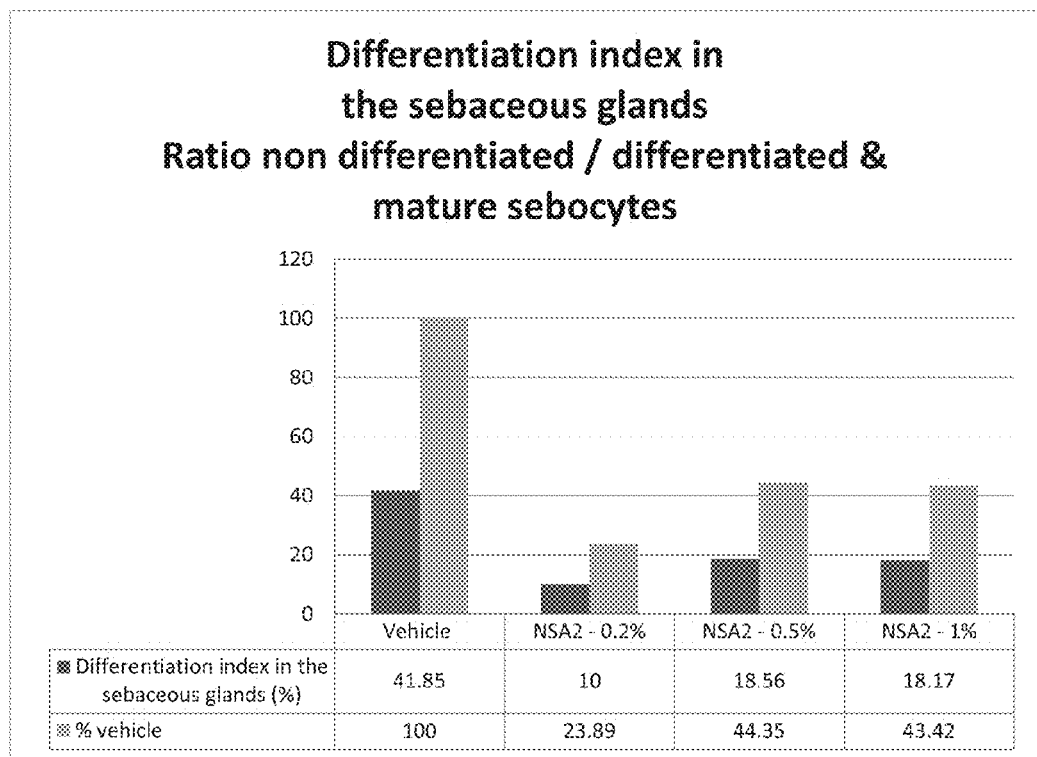

FIG. 6 shows the differentiation index in the sebaceous glands subsequent to treatment with NSA-2 at three different concentrations for a 3 week period (5 application days per week).

Figure 7:
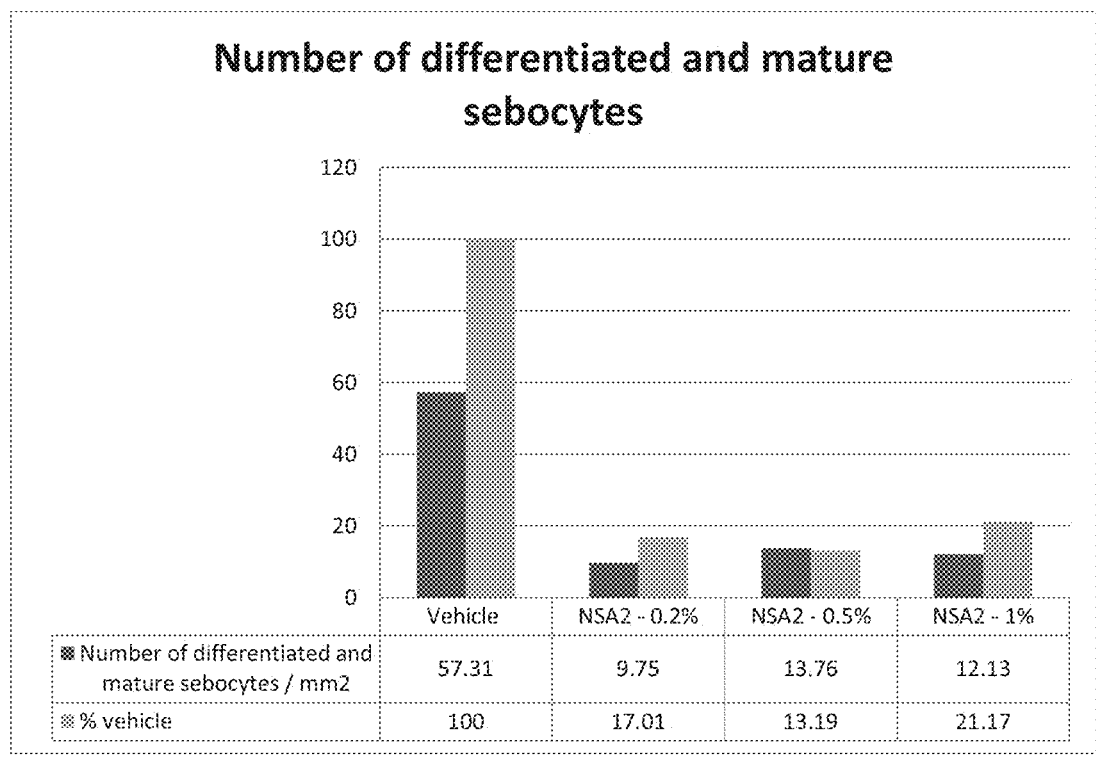

FIG. 7 shows the number of differentiated and mature sebocytes subsequent to treatment with NSA-2 at three different concentrations.

Figure 8:
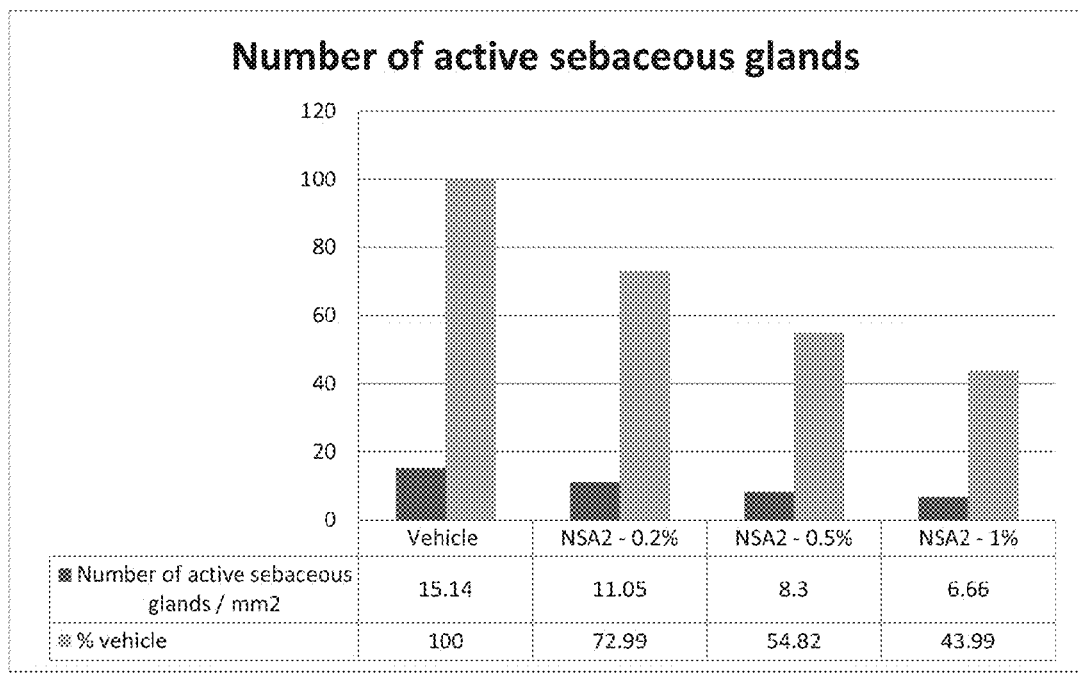

FIG. 8 shows the number of active sebaceous glands subsequent to treatment with NSA-2 at three different concentrations.

DETAILED DESCRIPTION OF THE INVENTION

The subject invention provides a method of treating acne in a subject which comprises topically and periodically applying to the subject's acne a composition comprising 3-phenyl-1-benzo[f]chromen-1-one and a pharmaceutically acceptable carrier, wherein the 3-phenyl-1-benzo[f]chromen-1-one is present in the composition in an amount effective to treat the subject's acne.

In one embodiment, 3-phenyl-1-benzo[f]chromen-1-one, also known as beta-naphthoflavone, is present in the composition at a concentration between about 0.005% and about 5% by weight. In another embodiment, 3-phenyl-1-benzo[f]chromen-1-one is present in the composition at a concentration between about 0.1% and about 2.5% by weight. In yet another embodiment, 3-phenyl-1-benzo[f]chromen-1-one is present in the composition at a concentration of about 0.1% by weight. In still other embodiments, 3-phenyl-1-benzo[f]chromen-1-one is present in the composition at a concentration of about 0.25% by weight, about 0.5% by weight, about 1% by weight, about 2% by weight, or about 5% by weight.

In some embodiments, the pharmaceutically acceptable carrier comprises ethanol.

In other embodiments, the pharmaceutically acceptable carrier comprises polyethylene glycol having an average molecular weight between 200 g/mol and 1000 g/mol. In one such embodiment, the polyethylene glycol has an average molecular weight of about 400 g/mol.

In yet other embodiments, the pharmaceutically acceptable carrier comprises a mixture of ethanol and polyethylene glycol in a ratio from 5:1 to 1:5 by volume, for example, between 2:1 and 1:2 by volume, particularly about 1:1 by volume.

In some embodiments, the pharmaceutical composition is a solution and comprises 3-phenyl-1-benzo[f]chromen-1-one at a concentration between 0.005 g and 1.0 g 3-phenyl-1-benzo[f]chromen-1-one per 100 mL of the composition and the pharmaceutically acceptable carrier comprises a mixture of ethanol and polyethylene glycol having an average molecular weight of about 400 g/mol in a ratio of about 1:1 by volume. In another embodiment, the concentration of 3-phenyl-1-benzo[f]chromen-1-one is between 0.05 g and 0.5 g. In yet another embodiment, the 3-phenyl-1-benzo[f]chromen-1-one is at a concentration of about 0.5 g, the polyethylene glycol has an average molecular weight of about 400 g/mol and the mixture of ethanol and polyethylene glycol is in a ratio of about 1:1 by volume.

In certain embodiments, the pharmaceutically acceptable carrier further comprises one or more of an alcohol, an anti-bacterial agent, a preservative, and a chelating agent.

In some embodiments, the pharmaceutical composition is in the form of a lotion, gel, cream, ointment, foam, solution, suspension, dispersion or impregnated dressing.

In some embodiments, the acne is facial acne; in other embodiments chest, back and/or shoulder acne, for example, the acne associated with *Propionibacterium* acnes or the acne is associated with a high sebum secretion rate.

In some embodiments, 3-phenyl-1-benzo[f]chromen-1-one is topically applied daily. In other embodiments, 3-phenyl-1-benzo[f]chromen-1-one is topically applied only at night. In still other embodiments, 3-phenyl-1-benzo[f]chromen-1-one is topically applied twice or three times daily. In still further embodiments, 3-phenyl-1-benzo[f]chromen-1-one is topically applied every other day. In still other embodiments, 3-phenyl-1-benzo[f]chromen-1-one is topically applied weekly.

The subject invention also provides a method of treating a skin condition associated with abnormal sebum secretion or abnormal sebaceous gland function in a subject which comprises topically and periodically applying to an area of the subject's skin affected by the skin condition a composition comprising 3-phenyl-1-benzo[f]chromen-1-one and a pharmaceutically acceptable carrier, wherein the 3-phenyl-1-benzo[f]chromen-1-one is present in the composition in an amount effective to treat the skin condition.

The skin condition may be any of oily skin, oily hair, shiny or greasy-looking skin, hyperseborrhea, seborrheic dermatitis, rosacea, sebaceous hyperplasia or sebaceous carcinoma. In some embodiments, the skin condition is seborrheic dermatitis. In other embodiments, the skin condition is rosacea. In yet other embodiments, the skin condition is hyperseborrhea, sebaceous hyperplasia, or sebaceous carcinoma.

In some embodiments, 3-phenyl-1-benzo[f]chromen-1-one is present in the composition at a concentration between about 0.005% and about 5% by weight. In other embodiments, 3-phenyl-1-benzo[f]chromen-1-one is present in the composition at a concentration between about 0.1% and about 2.5% by weight. In yet other embodiments, 3-phenyl-1-benzo[f]chromen-1-one is present in the composition at a concentration of about 0.1% by weight, about 0.25% by weight, about 0.5% by weight, about 1% by weight, about 2% by weight, or about 5% by weight.

In some embodiments, the pharmaceutically acceptable carrier comprises ethanol.

In other embodiments, the pharmaceutically acceptable carrier comprises polyethylene glycol having an average molecular weight between 200 g/mol and 1000 g/mol. In one such embodiment, the polyethylene glycol has an average molecular weight of about 400 g/mol.

In yet other embodiments, the pharmaceutically acceptable carrier comprises a mixture of ethanol and polyethylene glycol in a ratio from 5:1 to 1:5 by volume, for example, between 2:1 and 1:2 by volume, particularly about 1:1 by volume.

In some embodiments, the pharmaceutical composition is a solution and comprises 3-phenyl-1-benzo[f]chromen-1-one at a concentration between 0.005 g and 1.0 g 3-phenyl-1-benzo[f]chromen-1-one per 100 mL of the composition and the pharmaceutically acceptable carrier comprises a mixture of ethanol and polyethylene glycol having an average molecular weight of about 400 g/mol in a ratio of about 1:1 by volume. In another embodiment, the concentration of 3-phenyl-1-benzo[f]chromen-1-one is between 0.05 g and 0.5 g. In another embodiment, the ratio is between 2:1 and 1:2 by volume. In one such embodiment, the 3-phenyl-1-benzo[f]chromen-1-one is at a concentration of about 0.5 g, the polyethylene glycol has an average molecular weight of about 400 g/mol and the mixture of ethanol and polyethylene glycol is in a ratio of about 1:1 by volume.

In certain embodiments, the pharmaceutically acceptable carrier further comprises one or more of an alcohol, an anti-bacterial agent, a preservative, and a chelating agent.

In some embodiments, the pharmaceutical composition is in the form of a lotion, gel, cream, ointment, foam, solution, suspension, dispersion or impregnated dressing.

In some embodiments, the area of the subject's skin affected by the skin condition is on the face, chest, shoulders or back. In other embodiments, the skin condition is associated with *Propionibacterium* acnes and/or a high sebum secretion rate.

In some embodiments, 3-phenyl-1-benzo[f]chromen-1-one is topically applied daily. In other embodiments, 3-phenyl-1-benzo[f]chromen-1-one is topically applied only at night. In still other embodiments, 3-phenyl-1-benzo[f]chromen-1-one is topically applied twice or three times daily. In still further embodiments, 3-phenyl-1-benzo[f]chromen-1-one is topically applied every other day. In still other embodiments, 3-phenyl-1-benzo[f]chromen-1-one is topically applied weekly.

The subject invention also provides a composition comprising 3-phenyl-1-benzo[f]chromen-1-one and a pharmaceutically acceptable carrier, wherein the 3-phenyl-1-benzo[f]chromen-1-one is present at a concentration between about 0.005% and about 5% by weight.

In some embodiments, the 3-phenyl-1-benzo[f]chromen-1-one is present at a concentration between about 0.1% and about 2.5% by weight. In other embodiments, the 3-phenyl-1-benzo[f]chromen-1-one is present at a concentration of about 0.1% by weight. In yet other embodiments, the 3-phenyl-1-benzo[f]chromen-1-one is present at a concentration of about 0.25% by weight, about 0.5% by weight, about 1% by weight, about 2% by weight, or about 5% by weight.

In some embodiments, the pharmaceutically acceptable carrier comprises ethanol.

In other embodiments, the pharmaceutically acceptable carrier comprises polyethylene glycol having an average molecular weight between 200 g/mol and 1000 g/mol. In one such embodiment, the polyethylene glycol has an average molecular weight of about 400 g/mol.

In other embodiments, the pharmaceutically acceptable carrier comprises a mixture of ethanol and polyethylene glycol in a ratio from 5:1 and 1:5 by volume, for example, between 2:1 and 1:2 by volume, particularly, about 1:1 by volume.

In some embodiments, the pharmaceutical composition is a solution and comprises 3-phenyl-1-benzo[f]chromen-1-one at a concentration between 0.005 g and 1.0 g 3-phenyl-1-benzo[f]chromen-1-one per 100 mL of the composition and the pharmaceutically acceptable carrier comprises a mixture of ethanol and polyethylene glycol (having an average molecular weight of about 400 g/mol in a ratio of about 1:1 by volume. In other embodiments, the concentration of 3-phenyl-1-benzo[f]chromen-1-one is between 0.05 g and 0.5 g. In one such embodiment, the 3-phenyl-1-benzo[f]chromen-1-one is at a concentration of about 0.5 g, the polyethylene glycol has an average molecular weight of about 400 g/mol and the mixture of ethanol and polyethylene glycol is in a ratio of about 1:1 by volume.

In certain embodiments, the pharmaceutically acceptable carrier further comprises one or more of an alcohol, an anti-bacterial agent, a preservative, and a chelating agent.

In some embodiments, the pharmaceutical composition is in the form of a lotion, gel, cream, ointment, foam, solution, suspension, dispersion or impregnated dressing.

The subject invention also provides a method of predicting clinical responsiveness of a subject to treatment of acne by topical application of 3-phenyl-1H-benzo[f]chromen-1-one, the method comprising inducing CYP1A1 expression in the subject and evaluating the amount of CYP1A1 expressed so as to predict the clinical responsiveness of the subject.

In certain embodiments, the amount of CYP1A1 expressed has a positive correlation with clinical responsiveness.

The subject invention also provides a method of predicting clinical responsiveness of a subject to treatment of a skin condition associated with abnormal sebum secretion or abnormal sebaceous gland function by topical application of 3-phenyl-1H-benzo[f]chromen-1-one, the method comprising inducing CYP1A1 expression in the subject and evaluating the amount of CYP1A1 expressed to predict the clinical responsiveness of the subject.

In some embodiments, the skin condition is oily skin, oily hair, shiny or greasy-looking skin, hyperseborrhea, seborrheic dermatitis, rosacea, sebaceous hyperplasia or sebaceous carcinoma.

In certain embodiments, the amount of CYP1A1 expressed has a positive correlation with clinical responsiveness.

The subject also relates to a method of triaging or sorting and selecting substances in order to better determine their capacity for sebosuppressive activity in topical or local skin treatments, comprising an in vivo test, the said in vivo test comprising the following steps:
  a) choosing a substance from amongst sebum reducing AhR pathway agonists;
  b) choosing a mammal in which the CYP1A1 gene can be induced in the skin;
  c) treating a part of the skin of said mammal, chosen in relation to the localization of sebaceous glands thereof, via a topical route, with a composition containing the said substance, following a dose response vs. time protocol;
  d) examining by means of immune-histological staining the expression of CYP1A1 in the sebaceous glands of the chosen said mammal treated locally on the skin; and
  e) selecting said substance in relation to the sequence of onset of immunohistochemical labelling vs. time in several different types (compartments) of cells of the said sebaceous glands The said sebum reducing AhR pathway agonists to be tested are preferably chosen from among known AhR agonists or first determined to be an AhR agonist by at least one suitable in vitro test, for example first screening using the CALUX (He et al. 2011) and/or EROD tests (Zamaratskaia et al. (2009), Behnisch et al. (2001),), to determine both potency and the degree of maximum induction, combined with the understanding or demonstration of a short in vivo half-life by standard methods known to those skilled in the art.

For testing in vivo, before man, rodents, in particular, the mouse, are preferred mammals for this purpose, more preferably the murine C57BL/6 strain.

As far as the site of application of the compounds to rodents is concerned, the skin of the ears, which are known to contain multiple sebaceous glands, are particularly preferred. Being well suited to this type of analysis they are also a locale where the CYP1A1 gene is likely to be induced.

According to a further embodiment, the ears of the said mice are treated via the topical route, then sampled vs. time, and the expression of CYP1A1 is examined by immunohistochemical analysis using an antibody. In particular, but not limited thereto, the antibody used may be the rabbit anti-rat CYP1A1 polyclonal antibody (Millipore AB1247).

In such an embodiment, the examination of the expression of CYP1A1 in the sebaceous glands may comprise:
  a) examination of the isthmus region, in particular examination of the progenitor cells (see Jensen et al. 2009, Niemann et al. 2012);
  b) examination of the peripheral regions of the gland, particular examination of the undifferentiated cells;
  c) examination of the intermedia region of the gland, particular examination of the differentiated cells; and/or
  d) examination of the central region of the gland, in particular examination of the mature cells.

The substance is considered active if the said in vivo test exhibits immunohistochemical staining in the plurality of relevant cell types indicated above within a determined time period;

After examining these four cell types, the said substance can be selected if the expression of CYP1A1 is labeled in at least two cell types after one week's treatment.

After examining these four cell types, the said substance is preferably selected if the expression of CYP1A1 is labelled in all four cell types after one week's treatment.

Further selection can be made by treating said mammal with a potential sebum reducing AhR pathway agonist and measuring markers of actual sebum production by standard methods, including squalene and/or waxy esters (e.g., Smith et al. (2008), Miyazaki et al. (2001)).

According to a further embodiment of the present invention, an object of the invention is a composition for treating and/or preventing skin diseases of a human being, in particular the associated skin conditions of acne, seborrheic dermatitis and rosacea, wherein the composition is able to treat and/or prevent hyperseborrhea by means of topical or local application of said composition on the skin, and composition comprising an active substance selected from the group consisting of AhR pathway agonists having:
  a) an ability to activate one or more components of the sebum reducing AhR pathway;
  b) an ability to modulate a gene regulated by the AhR pathway;
  c) a short half-life in the human organism, either predicted from standard mammalian pharmacokinetic studies or actually determined, of less than 24 hours; preferably less than 4 hrs
  d) a measureable positive effect on a recognized criterion of sebum reduction.

A presently preferred embodiment of the invention is rutecarpine, a pharmaceutically acceptable salt of rutecarpine, or an herbal (plant/fruit) extract comprising rutecarpine as the active substance in a sebosuppressive composition for topical use.

Another presently preferred embodiment of the invention is 3-phenyl-1H-benzo[f]chromen-1-one, as the active substance in a sebosuppressive composition for topical use.

According to yet a further aspect of the invention, an object of the invention is a method for treating and/or preventing skin diseases of a human being, such as acne, seborrheic dermatitis and rosacea, comprising providing a composition that is able to treat and/or prevent hyperseborrhea by means of topical application of said composition on the skin, said composition comprising an active substance selected from the group consisting of sebum reducing AhR pathway agonists having:
  a) an ability to act as a sebum reducing AhR pathway agonist;
  b) an ability to modulate a gene regulated by the AhR pathway;
  c) a short half-life in the human organism, either predicted from standard mammalian pharmacokinetic studies or actually determined of less than 24 hours; more preferably less than 4 hours;
  d) a measureable positive effect on a recognized criterion of sebum reduction;
  e) and wherein said active substance is positively selected by an in vivo test as defined above;
  f) and wherein said composition is administered topically to said human being.

A particular object of the invention is thus a process for treating and/or preventing hyperseborrhea-induced skin conditions in a human being, comprising providing a composition suitable for topical application on the skin, wherein said composition contains 3-phenyl-1H-benzo[f]chromen-1-one as the active substance, and administering said composition topically or locally to said human being.

For all of the foregoing embodiments, each embodiment disclosed herein is contemplated as being applicable to each of the other disclosed embodiments.

Terms

As used herein, and unless stated otherwise, each of the following terms shall have the definition set forth below.

As used herein, the term "sebaceous glands" refers to microscopic glands in the skin that secrete an oily/waxy matter, called sebum, to lubricate and waterproof the skin and hair of mammals. In humans, they are found in greatest abundance on the face and scalp, though they are distributed throughout all skin sites except the palms and soles.

As used herein, the term "skin" refers to the outer coverage of the body. In humans, it is the largest organ of the integumentary system. The skin has multiple layers of ectodermal tissue and guards the underlying muscles, bones, ligaments and internal organs. Human skin is similar to that of most other mammals, except that it is not protected by fur. Though nearly all human skin is covered with hair follicles, it can appear hairless. The adjective cutaneous means "of the skin" (from Latin cutis, skin).

As used herein, the term "dermatoporosis" refers to a new concept proposed to cover different manifestations and implications of chronic cutaneous insufficiency/fragility syndrome. This emerging syndrome extends beyond cosmetics and appearance and is considered to be the functional face of skin aging (Kaya et al. (2007)).

As used herein, the term "acne" refers to acne vulgaris, a common human skin disease, characterized by areas of skin with seborrhea (scaly red skin), comedones (blackheads and whiteheads), papules (pinheads), nodules (large papules), pimples, papulopustules and possible scarring. Acne affects mostly skin with the densest population of sebaceous glands; these areas include the face, the upper part of the chest, and the back. Severe acne is inflammatory, but acne can also manifest in non-inflammatory forms. The lesions are caused by changes in pilosebaceous units, skin structures consisting of hair follicle and its associated sebaceous gland, changes that require androgen stimulation.

As used herein, the term EROD refers to the ethoxyreorufin-O-deethylase (EROD) assay which monitors the induction of the xenobiotic-metabolizing enzyme cytochrome P-450 1A1(CYP1A1) and is a widely used as a reporter for measuring activation of the AhR in vitro (Zamaratskaia et al. (2009), Behnisch et al. (2001),)

As used herein, the term CALUX refers to Chemical-Activated Luciferase Gene Expression (CALUX). The CALUX Assay is a dioxin screening bioassay categorized as a reporter-gene assay. It has been approved as an official analysis method by the US EPA in 2007 (Method 4435) (He et al. (2011))

As used herein, the term CYP1A1 refers to Cytochrome P450, family 1, subfamily A, polypeptide 1. CYP1A1 is a protein that in humans is encoded by the CYP1A1 gene. The protein is a member of the cytochrome P450 superfamily of enzymes, CYP1A1 is involved in phase I xenobiotic and drug metabolism (e.g., Monostory et al. (2009), Nerbert and Dalton (2006), Zhou et al. (2009)).

As used herein, the term "treating" or "treatment" of any condition, disease or disorder refers, in some embodiments, to ameliorating the disease, disorder, or condition (i.e., arresting or reducing the development of the disease, disorder, or condition, or at least one of the clinical symptoms thereof). In other embodiments "treating" or "treatment" refers to ameliorating at least one physical parameter, which may or may not be discernible by the subject, including physical parameters that are undesired but not clinically significant. In yet other embodiments, "treating" or "treatment" refers to inhibiting the disease, disorder, or condition, either physically, (e.g., stabilization of a discernible symptom), physiologically, (e.g., stabilization of physical parameter) or both. In yet other embodiments, "treating" or "treatment" refers to preventing or to delaying the onset of the disease, disorder, or condition.

As used herein, the term "therapeutically effective amount" or "effective amount" means the amount of a composition, compound, therapy, or course of treatment that, when administered to a subject for treating a disease, disorder, or condition, is sufficient to effect such treatment for the disease, disorder, or condition. The "therapeutically effective amount" will vary depending on the composition, the compound, the therapy, the course of treatment, the disease, disorder, or condition, and its severity and the age, weight, etc., of the subject to be treated.

As used herein, sebum reducing AhR pathway agonists are compounds that by activating one or more components of the AhR pathway, are capable of reducing sebum levels in the skin, when applied topically, locally or systemically.

In the scope of the embodiments, the AhR ligands described herein include further forms of the compounds such as pharmaceutically acceptable salts, solvates (including hydrates), amorphous phases, partially crystalline and crystalline forms (including all polymorphs), prodrugs, metabolites, N-oxides, isotopically-labeled, epimers, pure epimers, epimer mixtures, enantiomers including but not limited to single enantiomers and enantiomeric diastereomers, meso compounds, stereoisomers, racemic mixtures and diasteroisomeric mixtures. AhR ligand compounds described herein having one or more double bonds include cis/trans isomers, E/Z isomers and geometric isomers. AhR ligand compounds described herein can be prepared as pharmaceutically acceptable salts formed when an acidic proton present in the parent compound either is replaced by a metal ion, for example an alkali metal ion, an alkaline earth ion, or an aluminum ion; or coordinates with an organic base. AhR ligand compounds described herein can also be prepared as pharmaceutically acceptable salts when a basic function present in the parent compound coordinates with a mineral acid or an organic acid. AhR ligand compounds can also be described herein as being prepared as pharmaceutically acceptable complexes or co-crystals whereby the complex or co-crystal confers modified physical properties of solubility, dissolution rate or permeability. In addition, the salt forms of the disclosed compounds can be prepared using salts of the starting material or intermediates.

In some embodiments, the AhR pathway agonist compounds described herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated.

In some embodiments, substitution with deuterium affords certain therapeutic advantages resulting from greater metabolic stability, such as, for example, increased in vivo half-life or reduced dosage requirements. Throughout the specification, groups and substituents thereof can be chosen by one skilled in the field to provide stable moieties and compounds.

This invention will be better understood by reference to the Experimental Details which follow, but those skilled in the art will readily appreciate that the specific experiments detailed are only illustrative of the invention as described more fully in the claims which follow thereafter.

Experimental Details

Description of an Embodiment of the Triage or Sorting Method

According to the state of the art, the biological activity triggered by the topical or systemic administration of the ligand should be uniform in all parts of the body which express the receptor, provided that the ligand is diffused in these parts in sufficient quantity and in a non-metabolized active form, such as seen with the retinoic acid receptor (RAR) or the vitamin D receptor (Milde et al (1991); Reichrath et al (1997)).

In this case, the application of AhR pathway agonist to the skin should activate the biochemical pathways linked to this receptor uniformly, first in the surface layers of the epidermis, and then progressively, correlating with the entry gradient of the ligand into the deeper layers of the epidermis, possibly the dermis and adnexa, hairs and sebaceous glands. It is known that the AhR receptor is expressed in all these compartments of the skin (Ikuta et al. 2009).

Yet, surprisingly, the applicant has found that the topical application to the skin of a sebum reducing AhR pathway agonist which is capable of acting as a sebosuppressive agent, activates the pathway of this receptor in focal manner on the sebaceous glands starting with the progenitor cells, i.e. the sebaceous stem cells located in the isthmic region of the pilosebaceous unit, followed in sequence by the non-differentiated sebaceous cells, the differentiated sebaceous cells, and finally the mature cells. These observations are illustrated in FIGS. 1 and 2.

Yet more surprisingly, the ligands endowed with the strongest sebosuppressive activity are those which, without necessarily being the most active during in vitro activation tests of the AhR receptors, follow this sequence of activation in situ at an early stage, rapidly and completely as shown by Tables 1 and 2.

These observations are counter-intuitive to those of M. J. Rowe et al. (Rowe et al. (2008)) who have shown that in a transgenic mouse with a CYP1A1-GFP promoter the biological activity induced by an AhR pathway agonist administered via the systemic route could be localized to the sebaceous glands, but in a uniform manner within the latter:

a) First, according to the applicant's observations, the administration route is transcutaneous, and the order of distribution is fully unexpected according to the sequence of transepidermal diffusion explained above. In the work conducted by Rowe et al., the ligand, 3-methylcholanthrene, is administered via the systemic route which results in access to the skin via the blood. The distribution of a lipophilic ligand in the sebaceous gland in therefore not surprising;

b) Second, and more specifically, the essential activation sequence of the present invention, i.e. progenitor cells>undifferentiated cells>differentiated cells>mature cells, was not observed by Rowe et al. (Rowe et al. (2008)) who demonstrate diffuse biological activity in the region of the sebaceous glands. The work of Rowe, et al. would not have allowed either the determination or the suggestion of the method for triaging/sorting sebosuppressive ligands which is the subject of this invention.

c) Third, and more specifically, Rowe et al. did not measure sebum levels or make any measurement of lipid production.

d) Fourth, Rowe et al. did not mention either 3-phenyl-1-benzo[f]chromen-1-one or rutecarpine or suggest their use in the treatment of acne.

Demonstration of the Sequential Activation of Sebum Reducing AhR Pathway Agonists in the Focal Regions of the Sebaceous Glands The embodiment described here entails treating the ears of C57BL/6 mice via the topical route, following established protocols to determine dose-response and time-response relationships, with sebum reducing AhR pathway agonists previously characterized for their in vivo activation of the receptor, using, for example the EROD and CALUX methods which are widely used in this field (see Table 1).

TABLE 1

| Compound | CALUX Efficiency | | EROD Efficiency | | Conc. tested in the Mouse Model mM* | Focal expression of AhR activation (CYP1A1) | | | | Sebogenesis inhibition index in mice % control | Human activity |
|---|---|---|---|---|---|---|---|---|---|---|---|
| | Conc. μM | % of 10 nM TCDD efficiency | Conc. μM | % of 10 nM TCDD efficiency | | Progenitor cells Stage 1 | Undifferentiated Stage 2 | Differentiated Stage 3 | Mature Stage 4 | | |
| NSA 1 | 10 | 78 | 1 | 25 | 12 | ▨▨▨ | ▨▨▨ | ooo | ooo | 28 | ▨ |
| NSA 2 | 5 | 13 | 10 | 20 | 45 | ▨▨▨ | ▨▨▨ | ▨▨▨ | ▨▨▨ | 90 | ▨▨▨ |
| NSA 3 | 0.01 | 100 | 0.01 | 100 | 0.0062 | ▨▨▨ | ▨▨▨ | ▨▨▨ | ▨▨▨ | 97 | ▨▨▨ |
| NSA 4 | 0.1 | 76 | 0.1 | 60 | 0.035 | ▨▨▨ | ▨▨▨ | ooo | ooo | 8 | NT |
| NSA 5 | 100 | 32 | 100 | 30 | 41 | ▨▨▨ | ooo | ooo | ooo | 11 | NT |
| NSA 6 | 100 | 58 | 100 | 10 | 21 | ▨▨▨ | ooo | ooo | ooo | 16 | NT |
| NSA 7 | 100 | 17 | | | 232 | ▨▨▨ | ooo | ooo | ooo | 5 | o |

NT = NOT TESTED
ooo and o = No activity
▨▨▨ Active
▨ Weak activity
*= corresponding to 1% in acetone
NSA-1 and NSA-2 were both tested in man at 0.5%
NSA-7 was tested in man at 8%.

Table 1 shows the correlations between in vitro tests, in vivo tests according to the invention, and clinical examination of the subosupressive activity in man of the ligands from FIG. 3.

Following topical treatment, the ears are sampled, and CYP1A1 expression is examined by immunohistochemical analysis using a specific antibody.

The study diagrammed in FIG. 1 and for which photomicrographs are provided in FIG. 2 entailed treating mice daily for one week with a topical AhR pathway agonist, with ears taken for examination at Day 7. Ears were recovered and fixed in formalin, paraffin embedded and then sections were prepared and positioned on slides for immunohistochemical staining. The specific antibody used in this instance was rabbit anti-rat CYP1A1 polyclonal antibody (Millipore AB1247). The AhR pathway agonists used in the example in FIG. 2 were as follows:

1B) 6-formylindolo[3,2-b]carbozole (NSA4/FICZ);
2B) 8,13-Dihydroindolo[2',3':3,4]pyrido[2,1-b]quinazolin-5(7H)-one (NSA1/rutecarpine);
3B) 3-phenyl-1H-benzo[f]chromen-1-one (NSA2);
4B)_2,3,7,8-tetrachlorodibenzo-p-dioxin (NSA3/TCDD).

NSA2 was used at a concentration of 37 mM, NSA4 was used at 35 μM, NSA1 at 12 mM, and NSA3 at 6.2 μM.

Photomicrographs were taken on a Zeiss microscope at a magnification of 250-fold for photos 1B, 2B, 3B, 4B of FIG. 2 and at a magnification of 400-fold for Part 10 of the Figure.

FIG. 1 shows diagrammatically the different types of labelling observed. A positive result from immunohistochemistry, i.e. the cells stained brown as would be shown in color originals of the black and white illustrations of FIG. 2, indicates that the region expresses the CYP1A1 protein. Results are summarized as follows:
   a) In the basal state the CYP1A1 protein is not detectable.
   b) In every case in which the AhR pathway agonists were used, it led to positive staining by CYP1A1 immuno-histochemistry. The first region in time to be stained, indicating an increase in the CYP1A1 protein induced by activation of the AhR receptor, is the region of the isthmus where the progenitor cells of the sebaceous glands are located (FIG. 1—1A and FIG. 2—1B).
   c) Stage 1 corresponds to multi-potent clonogenic cells, in other words to the sebaceous stem cells (Frances D and Niemann C (2012)). In addition to the particular topography of the isthmus region, these cells are characterized by the expression of L-RIG1, a marker of isthmic multi-potent clonogenic cells (Jensen et al. (2009),). Using double CYP1A1 and L-RIG1 staining it was also possible to show that the cells activated by the topically administered AhR pathway agonist effectively correspond to this population at this isthmic region.
   d) Stage 2 is the extension of CYP1A1 staining to undifferentiated cells which do not contain lipids and in general are located on the periphery of the sebaceous gland (FIG. 1—2A and FIG. 2—2B).
   e) Stage 3 is the further extension of CYP1A1 staining to differentiated cells which contain lipids and are in general located at the intermediate part of the sebaceous gland (FIG. 1—3A and FIG. 2—3B).
   f) Stage 4 is the further extension of CYP1A1 staining to mature cells which contain lipids and in general are located at the central part of the sebaceous gland (FIG. 1—4A and FIG. 2—4B).

Correlation Between the Sequential Activation Stages and the Sebosuppressive Properties of the Ligand Table 1 indicates the correlation between the stages of focal activation expression, the index of sebum inhibition, and the effect on human skin. The sebum inhibition index is calculated by counting the number of mature and differentiated cells in relation to the total number of cells in the sebaceous glands. A decrease in mature and differentiated cells indicates blocking of sebogenesis. The effect on human skin is determined by sebumetric examination using what is known as the "casual level" (Dobrev (2007)).

In FIG. 3 and Tables 1 and 2, the abbreviations used refer to the following chemicals:
   a) NSA1: 8,13-Dihydroindolo[2',3':3,4]pyrido[2,1-b]quinazolin-5(7H)-one (rutecarpine)
   b) NSA2: 3-phenyl-1H-benzo[f]chromen-1-one
   c) NSA3: 2,3,7,8-tetrachlorodibenzo-p-dioxin(TCDD)
   d) NSA4: 6-formylindolo[3,2-b]carbazole(FICZ)
   e) NSA5: 2-[(E)-2-(3,4-dihydroxyphenyl)ethenyl]-6-hydroxypyran-4-one (Hispidine)
   f) NSA6: 9H-Z-carboline(Beta-carboline)
   g) NSA7: (S)-5-methoxy-2-[(4-methoxy-3,5-dimethylpyridin-2-yl)methylsulfinyl]-3H-benzoimidazole (Esomeprazole)
   h) NSA8: 2-phenyl-4H-benzo[h]chromen-4-one
   i) NSA9: 2-phenyl-4H-chromen-4-one A comparison between FIG. 3 and Table 1 shows that two AhR pathway agonists, namely NSA-2 (3-phenyl-1H-benzo[f]chromen-1-one) and NSA-3 (TCDD), which activate the AhR pathway in the four cell sub-populations within a period of less than one week, are also those which display the strongest sebosuppressive activity in man. For testing in the mouse model, all compounds were tested at 1% in acetone. NSA-1 (Rutecarpine), while more effective than NAS-2 in in vitro activation assays, activates the AhR pathway in two of the cell sub-populations in mice, also has potentially useful sebosuppressive activity in man when tested at the same concentrations (0.5%), although weaker than that of NSA-2. On the other hand, NSA-7, which only activates the AhR receptor pathways in Stage One of the cell sub-populations, shows no sebosuppressive activity in man, even at 8%, even though its ability to activate AhR in vitro appears similar to NSA-2.

Description of Sebosuppressive Property of 3-phenyl-1H-benzo[f]chromen-1-one and Related Structural Analogs The sebosuppressive activity of 3-phenyl-1H-benzo[f]chromen-1-one was compared with that of 2-phenyl-4H-benzo[h]chromen-4-one and 2-phenyl-4H-chromen-4-one under the same test conditions as those described above, namely in vitro test, the mouse in vivo tests as described in this invention and by clinical examination in man. The results for in vitro activation and focal expression of CYP1A1 in mice are given in Table 2, below. It can be seen that NSA-2 (3-phenyl-1H-benzo[f]chromen-1-one) demonstrates agonist activity in the sebaceous glands in a similar manner to the most active AhR agonist (TCDD), while 2-phenyl-4H-benzo[h]chromen-4-one and 2-phenyl-4H-chromen-4-one do not have these effects. Without wishing to be bound by any theory, it would appear that this capacity for tissue distribution is somehow dissociated from the agonist activity of the molecule for the AhR receptor as determined by the EROD and CALUX assays, since molecules having much greater activity in those assays, such as NSA4 (FICZ) have limited distribution in the sebaceous glands when compared with NSA-2. When the three compounds (NSA-2, NSA-8 and NSA-9) were tested in man at 0.5% neither 2-phenyl-4H-benzo[h]chromen-4-one nor 2-phenyl-4H-chromen-4-one exhibited any reduction in sebum (as determined by sebutape and clinical observations). Only NSA-2 was active in reducing sebum. In combination with other properties set forth below, this property of sequentially targeting the sebaceous glands correlates with the sought-after therapeutic effects in humans.

Table 2 shows the activity of TCDD and three other compounds (NSA-2, NSA-8 and NSA-9) in both cell based in vitro tests and in vivo tests according to the invention.

|  | CALUX efficiency | | EROD efficiency | | Focal expression of AhR activation in vivo (CYP1A1) | | | |
| --- | --- | --- | --- | --- | --- | --- | --- | --- |
|  | Concentration ($\mu$M) | % of 10 nM TCDD | Concentration ($\mu$M) | % of 10 nM TCDD | Progenitor Stage 1 | Non-differentiated Stage 2 | Differentiated Stage 3 | Mature Stage 4 |
| TCDD (NSA-3) | 0.01 | 100 | 0.01 | 100 | ☒☒☒ | ☒☒☒ | ☒☒☒ | ☒☒☒ |
| 3-phenyl-1H-benzo[f]chromen-1-one (NSA-2) | 10 | (7) | 10 | 20 | ☒☒☒ | ☒☒☒ | ☒☒☒ | ☒☒☒ |

-continued

| | CALUX efficiency | | EROD efficiency | | Focal expression of AhR activation in vivo (CYP1A1) | | | |
|---|---|---|---|---|---|---|---|---|
| | Concentration ($\mu$M) | % of 10 nM TCDD | Concentration ($\mu$M) | % of 10 nM TCDD | Progenitor Stage 1 | Non-differentiated Stage 2 | Differentiated Stage 3 | Mature Stage 4 |
| 2-phenyl-4H-benzo[h]chromen-4-one (NSA-8) | — | — | 100 | 0.7 | ooo | ooo | ooo | ooo |
| 2-phenyl-4H-chromen-4-one (NSA-9) | 100 | 10 | 100 | 11 | ☒☒☒ | ooo | ooo | ooo |

In mice the three compounds (NSA2, NSA8 and NSA9) were tested at 0.5% in acetone.
TCDD (NSA-3) was tested on mice at 0.0005%.
ooo = No activity
☒☒☒ = Active FIG. 4 shows the results of experiments in which the ears of C57BL/6 mice were treated with the three different compounds (NSA-2, NSA-8 and NSA-9) above at 0.5% in acetone for five weeks. The reference substance (positive control) was TCDD at a concentration 1000 times lower (0.0005%). At the end of that time the animals were sacrificed and the ears removed for further analysis.

To generate the data for FIG. 4, after extraction of RNA by standard methods, Real-Time QRT-PCR reactions were performed followed by analysis for the presence of mRNA corresponding to three major enzymes (fatty acid desaturase 2 [FADS2], acyl-CoA wax alcohol acyltransferase 1 [AWAT1], and elongation of very long chain fatty acids protein 3 [ELOV3] in the production of sebaceous lipids. The results were compared with control mice treated with vehicle alone: FIG. 4 shows that among the three structurally related compounds tested (NSA-2, NSA-8 and NSA-9) only NSA-2 induced major inhibition of the mRNA expression encoding the three enzymes, whereas NSA-8 had a slightly stimulating effect whilst NSA-9 had no significant effect. NSA-2 strongly inhibited in mice the expression of the genes of key enzymes involved in the production of lipids characteristic of sebum such as AWAT1, ELOVL3, and FADS2, which at least partly accounts for the sebosuppressive effects of this compound. The degree of specific gene suppression seen with NSA-2 is equivalent to that seen with the structurally unrelated compound NSA-3 (TODD).

The Relationship between 3-phenyl-1H-benzo[f]chromen-1-one Dose and Sebosuppressive Effects The dosing regimen of NSA-2 which achieves significant suppression of sebogenesis must be carefully defined, in particular to ensure good tolerability and prevent the theoretical risk onset of cysts of MADISH type. Recall again, TCDD can act as a pM agonist of AhR and has a half-life measureable in years. In contrast, NSA-2 has a half-life in rodents reported at less than 45 mins (Adedoyin et al. (1993)).

In addition, even at 10 $\mu$M, NSA-2, as measured in the standard EROD assay, only activates AhR to 10-20% of the level of induction seen with 0.01 $\mu$M TCDD. These essential observations were made in several phases as follows:

Dose Effect in Mice:

Preliminary studies showed good tolerability of NSA-2 at all doses tested and activity in the sequential in vivo activation tests in mice described above. For these dose-effects tests, C57BL/6 mice were treated for three to five weeks, five days per week on the ears and in three concentrations, namely 0.1, 0.5, and 1% of NSA-2. The sebosuppressive effect was analyzed at the third week although expression thereof starts after one week. FIGS. 5-8 show very marked effects which few substances other than TCDD are able to induce in this model both regarding the total number of active sebaceous glands (FIG. 8), the relative surfaces occupied by the sebaceous glands (FIG. 5) and the ratios between non-differentiated, differentiated and mature sebocytes (FIG. 6 and FIG. 7).

In particular, a reduction in the differentiated compartment of the gland was observed (FIG. 6 and FIG. 7), in good agreement with the suppressive effect on the genes encoding sebaceous lipogenesis enzymes (FIG. 4) since the differentiation of the sebocyte is defined by cytoplasmic lipid accumulation. Drug tolerability, in the absence of MADISH-type cyst production, was assessed after five weeks' treatment. No cystic lesion were observed with NSA-2 at any concentration tested. The blood assay of 3-phenyl-1H-benzo[f]chromen-1-one by HPLC in these mice did not detect any measureable level (5 nM sensitivity).

Tolerability and Effect of 3-phenyl-1H-benzo[f]chromen-1-one in Man:
  a) A stable 0.5% formulation of 3-phenyl-1H-benzo[f]chromen-1-one was defined.
  b) Formulation: 3-phenyl-1H-benzo[f]chromen-1-one 0.5 g/100 ml in ethanol/PEG 400 (1:1).
  c) Solvents: Ethanol EMSURE® Merck catalog number 1.00983, batch K42754183.
  d) Polyethylene Glycol (PEG) 400, Fluka catalog number 81 170, batch 260154 286 or PEG 400 Aldrich catalog number 202398.
  e) Stability: No degradation products were observed six months after preparation.
  f) Use in man: The formulation was applied once per day to the face in eleven patients suffering from intense seborrhea and not eligible for oral treatment with Isotretinoin, six with acne, four with rosacea and one with seborrheic dermatitis.
  g) No side effects were noted. In particular no clinical signs suggesting the onset of microcysts. This provides confirmation in humans of the safety of topical 3-phenyl-1H-benzo[f]chromen-1-one. This tolerability in man therefore amounts to original data of primary importance.
  h) The use of Sebutape® (CUDerm) patch test, to determine the amount of sebum produced in six individuals after treatment, indicated a level corresponding to the normal sebum production range.

CONCLUSION

This invention allows the rapid selection of candidate sebosuppressive molecules for therapeutic use in treating or preventing acne, seborrheic dermatitis and rosacea.

Persons skilled in the art will easily appreciate that the method of the invention could be implemented, without departing from the scope of the invention, in another laboratory mammal other than the C57BL/6 mouse strain, provided that the described activation sequence is reproduced.

The discrepancy between in vitro measurements of receptor activation and in vivo effects may reflect kinetic elements particular to the transport and diffusion of each molecule into the relevant tissues. The method which is the subject of this invention is therefore the first ever described which allows investigation of the specific targeting of different stages of the sebaceous cells within skin tissue by potential therapeutic molecules.

All of the ligands able to induce a significant sebosuppressive effect at the clinical level are those which, as early as the first week of treatment in mice, induced Cyp1A1 staining which exceeded Stage 2. The most active ligands reached Stage 4 as early as the first week of treatment (FIG. 3).

During the above-described tests, the 3-phenyl-1H-benzo [f]chromen-1-one selected after the in vivo tests according to the invention, confirmed its capacity for use as sebosuppressive treatment in the form of a topical application in the human being.

LIST OF REFERENCES

1. J. Abel et al. (2010) "An introduction to the molecular basics of aryl hydrocarbon receptor biology" *Biol. Chem.*, 391, 1235-1248
2. T. Ikuta et al. (2010) "B lymphocyte-induced maturation protein 1 is a novel target gene of aryl hydrocarbon receptor" *J. Derm. Sci.* 2010 June, 58 (3), 211-216.
3. PCT International Application Publication No. WO 2004/041758
4. PCT International Application Publication No. WO 2007/128725
5. U.S. Patent Application Publication No. 2009/0028804 A1
6. P. K. Mandal (2005) "Dioxin: a review of its environmental effects and its aryl hydrocarbon receptor biology" *J Comp Physiol B.*, 175(4), 221-230
7. J. H. Saurat et al. (2012), "The cutaneous lesions of dioxin exposure: Lessons from the poisoning of V. Yushchenko" *Toxicological Sciences*, 125, 310-317
8. U.S. Patent Application Publication No. 2010/0324109 A1
9. G. He et al. (2011), "Third-generation Ah receptor-responsive luciferase reporter plasmids: amplification of dioxin-responsive elements dramatically increases CALUX bioassay sensitivity and responsiveness *Toxicol. Sci.*, 123(2), 511-522
10. G. Zamaratskaia and V. Zlabek (2009) "EROD and MROD as Markers of Cytochrome P450 1A Activities in Hepatic Microsomes from Entire and Castrated Male Pigs" *Sensors*, 9, 2134-2147
11. Behnisch et al. (2001), "Bioanalytical screening methods for dioxins and dioxin-like compounds a review of bioassay/biomarker technology" *Environ. Int.* 27(5), 413-439
12. Jensen et al. (2009), "Lrig1 Expression Defines a Distinct Multipotent Stem Cell Population in Mammalian Epidermis" *Cell Stem cell*, 4(5), 427-439
13. C. Niemann and V. Horsley et al. (2012),"Development and homeostasis of the Sebaceous Gland" *Semin. Cell. Dev. Biol.*, 23(8), 928-936
14. K. R. Smith and D. M. Thiboutot (2008) "Sebaceous gland lipids: friend or foe?" *The Journal of Lipid Research*, 49, 271-281
15. Miyazaki et al. (2001), "Targeted Disruption of Stearoyl-CoA Desaturasel Gene in Mice Causes Atrophy of Sebaceous and Meibomian Glands and Depletion of Wax Esters in the Eyelid" *Am. Soc. Nutr. Sci.*, 131, 2260-2268
16. G. Kaya and J. H. Saurat (2007) "Dermatoporosis—A chronic cutaneous insufficiency/fragility syndrome: Cinico-pathological features, mechanisms, prevention and potential treatments" *Dermatology*, 215(4), 284-294
17. K. Monostory et al. (2009) "Hormonal regulation of CYP1A expression" *Drug Metab. Rev.*, 41(4), 547-572
18. D. W. Nebert and T. P. Dalton (2006), "The role of cytochrome P450 enzymes in endogenous signalling pathways and environmental carcinogenesis" *Nat. Rev. Cancer*, 2006, 6(12), 947-960.
19. S. F. Zhou et al. (2009), "Polymorphism of human cytochrome P450 enzymes and its clinical impact" *Drug Metab. Rev.* 2009, 4(2), 82-295.
20. P. Milde et al (1991) "Expression of 1,25-dihydroxyvitamin D3 receptors in normal and psoriatic skin" *J. Invest Dermatol.* 97(2), 230-9.
21. J. Reichrath et al., (1997) "Expression of retinoid-X receptors and retinoic acid receptors in normal human skin: an immunohistological evaluation" *The Histochemical Journal* 29(2), 127-133
22. M. J. Rowe et al. (2008) "Illuminating role of CYP1A1 in skin function" *J. Invest. Derm.*, 128, 1866-1868
23. D. Frances and C. Niemann (2012), "Stem cell dynamics in sebaceous gland morphogenesis in mouse skin" *Dev. Biol.*, 363 (1), 138-146
24. H. Dobrev (2007) "Clinical and instrumental study of the efficacy of a new sebum control cream" *Journal of Cosmetic Dermatology*, 6(2), 113-118
25. A. Adedoyin et al., (1993) "Time-dependent disposition of beta-naphthoflavone in the rat." *Pharmaceut Res*, 10, 35-43

What is claimed:

1. A topical composition comprising 3-phenyl-1-benzo[f] chromen-1-one and a pharmaceutically acceptable carrier, wherein the 3-phenyl-1-benzo[f]chromen-1-one is present at a concentration between about 0.1% and about 2.5% by weight and wherein the pharmaceutically acceptable carrier comprises polyethylene glycol having an average molecular weight between 200 g/mol and 1000 g/mol and an alcohol.

2. The composition of claim 1, wherein the 3-phenyl-1-benzo[f]chromen-1-one is present at a concentration of about 0.1% by weight.

3. The composition of claim 1, wherein the 3-phenyl-1-benzo[f]chromen-1-one is present at a concentration of about 0.25% by weight.

4. The composition of claim 1, wherein the 3-phenyl-1-benzo[f]chromen-1-one is present at a concentration of about 0.5% by weight.

5. The composition of claim 1, wherein the 3-phenyl-1-benzo[f]chromen-1-one is present at a concentration of about 1% by weight.

6. The composition of claim 1, wherein the 3-phenyl-1-benzo[f]chromen-1-one is present at a concentration of about 2% by weight.

7. The composition of claim 1, wherein the alcohol is ethanol.

8. The composition of claim 1, wherein the polyethylene glycol has an average molecular weight of about 400 g/mol.

9. The composition of claim 8, wherein the pharmaceutically acceptable carrier comprises a mixture of ethanol and polyethylene glycol in a ratio from 5:1 and 1:5 by volume.

10. The composition of claim 9, wherein the ratio of ethanol to polyethylene glycol is between 2:1 and 1:2 by volume.

11. The composition of claim 10, wherein the ratio of ethanol to polyethylene glycol is about 1:1 by volume.

12. The composition of claim 1, wherein the composition is a solution and comprises 3-phenyl-1-benzo[f]chromen-1-one at a concentration of about 0.5 g 3-phenyl-1-benzo[f]chromen-1-one per 100 mL of the composition and the pharmaceutically acceptable carrier comprises a mixture of ethanol and polyethylene glycol having an average molecular weight of about 400 g/mol in a ratio of about 1:1 by volume.

13. The composition of claim 1, wherein the pharmaceutically acceptable carrier further comprises one or more of an anti-bacterial agent, a preservative, and a chelating agent.

14. The composition of claim 1, wherein the composition is a lotion, gel, cream, ointment, foam, solution, suspension, dispersion or impregnated dressing.

15. A method of treating a skin condition associated with abnormal sebum secretion or abnormal sebaceous gland function in a subject which comprises topically and periodically applying to an area of subject's skin affected by the skin condition a composition comprising 3-phenyl-1-benzo[f]chromen-1-one and a pharmaceutically acceptable carrier, wherein the 3-phenyl-1-benzo[f]chromen-1-one is present in an amount effective to treat the skin condition and wherein the pharmaceutically acceptable carrier comprises polyethylene glycol having an average molecular weight between 200 g/mol and 1000 g/mol; wherein the skin condition is oily skin, oily hair, shiny or greasy-looking skin, hypersehorrhea, seborrheic dermatitis, rosacea, sebaceous hyperplasia or sebaceous carcinoma.

16. The method of claim 15, wherein the 3-phenyl-1-benzo[f]chromen-1-one is present in the composition at a concentration between about 0.005% and about 5% by weight.

17. The method of claim 16, wherein the 3-phenyl-1-benzo[f]chromen-1-one is present in the composition at a concentration between about 0.1% and about 2.5% by weight.

18. The method of claim 17, wherein the 3-phenyl-1-benzo[f]chromen-1-one is present in the composition at a concentration of about 0.1% by weight.

19. The method of claim 17, wherein the 3-phenyl-1-benzo[f]chromen-1-one is present in the composition at a concentration of about 0.25% by weight.

20. The method of claim 17, wherein the 3-phenyl-1-benzo[f]chromen-1-one is present in the composition at a concentration of about 0.5% by weight.

21. The method of claim 17, wherein the 3-phenyl-1-benzo[f]chromen-1-one is present in the composition at a concentration of about 1% by weight.

22. The method of claim 17, wherein the 3-phenyl-1-benzo[f]chromen-1-one is present in the composition at a concentration of about 2% by weight.

23. The method of claim 16, wherein the3-phenyl-1-benzo[f]chromen-1-one is present in the composition at a concentration of about 5% by weight.

24. The method of claim 15, wherein the polyethylene glycol has an average molecular weight of about 400 g/mol.

25. The method of claim 15, wherein the pharmaceutically acceptable carrier further comprises ethanol.

26. The method of claim 25, wherein the pharmaceutically acceptable carrier comprises a mixture of ethanol and polyethylene glycol in a ratio from 5:1 to 1:5 by volume.

27. The method of claim 26, wherein the ratio of ethanol to polyethylene glycol is between 2:1 and 1:2 by volume.

28. The method of claim 27, wherein the ratio of ethanol to polyethylene glycol is about 1:1 by volume.

29. The method of claim 15, wherein the composition is a solution and comprises 3-phenyl-1-benzo[f]chromen-1-one at a concentration between 0.005 g and 1.0 g 3-phenyl-1-benzo[f]chromen-1-one per 100 mL of the composition and the pharmaceutically acceptable carrier comprises a mixture of ethanol and polyethylene glycol having an average molecular weight of about 400 g/mol in a ratio of about 1:1 by volume.

30. The method of claim 29, wherein the 3-phenyl-1-benzo[f]chromen-1-one is at a concentration of about 0.5 g per 100 mL of the composition, the polyethylene glycol has an average molecular weight of about 400 g/mol and the mixture of ethanol and polyethylene glycol is in a ratio of about 1:1 by volume.

31. The method of claim 29, wherein the concentration of 3-phenyl-1-benzo[f]chromen-1-one is between 0.05 g and 0.5 g per 100 mL of composition.

32. The method of claim 15, wherein the pharmaceutically acceptable carrier further comprises one or more of an alcohol, an anti-bacterial agent, a preservative, and a chelating agent.

33. The method of claim 15, wherein the composition is a lotion, gel, cream, ointment, foam, solution, suspension, dispersion or impregnated dressing.

34. The method of claim 15, wherein the skin condition is seborrheic dermatitis.

35. The method of claim 15, wherein the skin condition is rosacea.

36. The method of claim 15, wherein the skin condition is hyperseborrhea.

37. The method of claim 15, wherein the skin condition is sebaceous hyperplasia.

38. The method of claim 15, wherein the skin condition is sebaceous carcinoma.

39. The method of claim 15, wherein 3-phenyl-1-benzo[f]chromen-1-one is topically applied daily.

40. The method of claim 39, wherein the composition is topically applied only at night.

41. The method of claim 39, wherein the composition is topically applied twice or three times daily.

42. The method of claim 15, wherein the composition is topically applied every other day.

43. The method of claim 15, wherein the composition is topically applied weekly.

* * * * *